United States Patent [19]
Apffel, Jr. et al.

[11] Patent Number: 5,223,131
[45] Date of Patent: Jun. 29, 1993

[54] APPARATUS FOR INTERFACING LIQUID CHROMATOGRAPHY-MASS SPECTROMETRY SYSTEMS

[75] Inventors: James A. Apffel, Jr., San Jose; Robert G. Nordman, Palo Alto, both of Calif.; Mirko Martich, Evanston, Ill.

[73] Assignee: Hewlett-Packard Company, Palo Alto, Calif.

[21] Appl. No.: 773,178

[22] Filed: Oct. 8, 1991

[51] Int. Cl.$^5$ .............................................. B01D 15/08
[52] U.S. Cl. .................................. 210/198.2; 210/656; 55/15; 55/17; 55/257.1; 55/261; 55/267; 55/277; 55/386; 250/288
[58] Field of Search .................. 55/15, 17, 257.1, 261, 55/267, 277, 386; 210/656, 748, 149, 177, 180, 182, 198.2; 250/281, 282, 288, 288 A

[56] References Cited

U.S. PATENT DOCUMENTS

| | | | |
|---|---|---|---|
| 4,160,161 | 7/1979 | Horton | 250/288 A |
| 4,531,056 | 7/1985 | Labowsky | 250/288 A |
| 4,629,478 | 12/1986 | Browner | 250/288 A |
| 4,863,491 | 9/1989 | Brandt | 210/198.2 |
| 4,980,057 | 12/1990 | Dorn | 250/288 A |

OTHER PUBLICATIONS

McLaughlin, "Particle Bean LC/MS for Drug Testing: Influence of Carrier Effect on Quantitation", 6th (Montreaux) Symposium on Liquid Chromatography/Mass Spectrometry (1990), p. 227.

Behymer, "Liquid Chromatography/Particle Beam/Mass Spectrometry of Polar Components of Environmental Interest", Anal. Chem., 62, 1990, pp. 1686–1690.

Bellar, "Investigation of Enhanced Ion Abundances from a Carrier Process in High Performance Liquid Chromatography Particle Beam Mass Spectrometry", J. Am. Soc. Mass Spectrom., 1, 1990, pp. 92–98.

Willoughby, "Monodispeese Aerosol Generation Interface, for Combining Liquid Chromatography with Mass Spectrometry", Anal. Chem., 56, 1984, pp. 2626–2631.

*Primary Examiner*—Ernest G. Therkorn

[57] ABSTRACT

Close coupled momentum separator with integral removable source volume for particle beam liquid chromatography/mass spectrometry is provided. The inventive PB LC/MS system comprises a momentum separator wherein the skimmers are designed to accommodate the particle beam conical dispersion so as to minimize the number of particles lost in the separator. In addition, the exit of the momentum separator is closely coupled to the entrance of the MS source volume. The PB LC/MS system demonstrates improved linearity in signal and enhanced sensitivity.

9 Claims, 3 Drawing Sheets

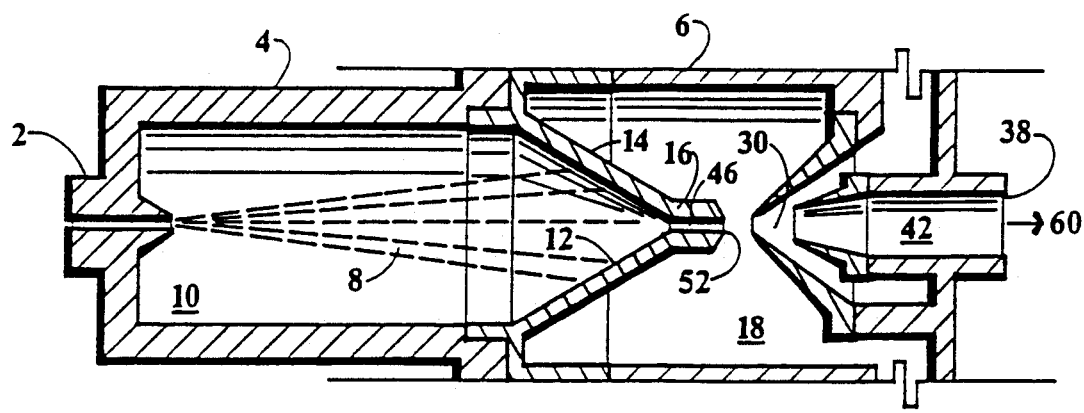
FIG._1.
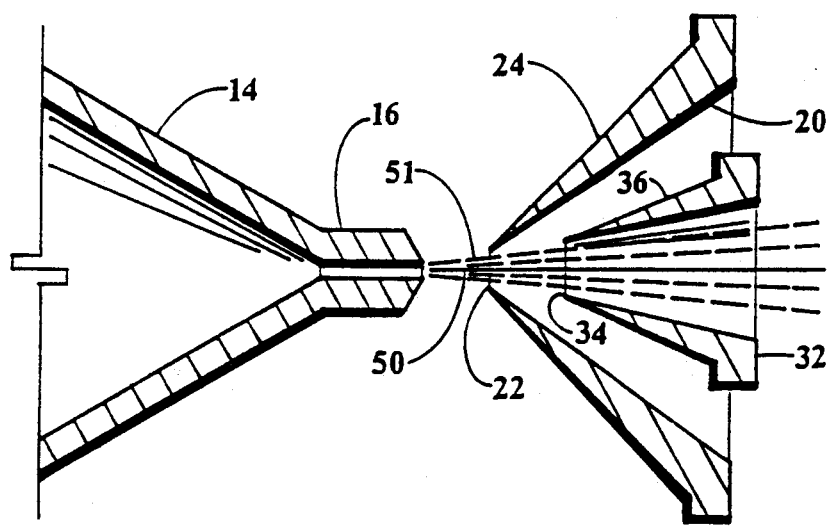
FIG._2.

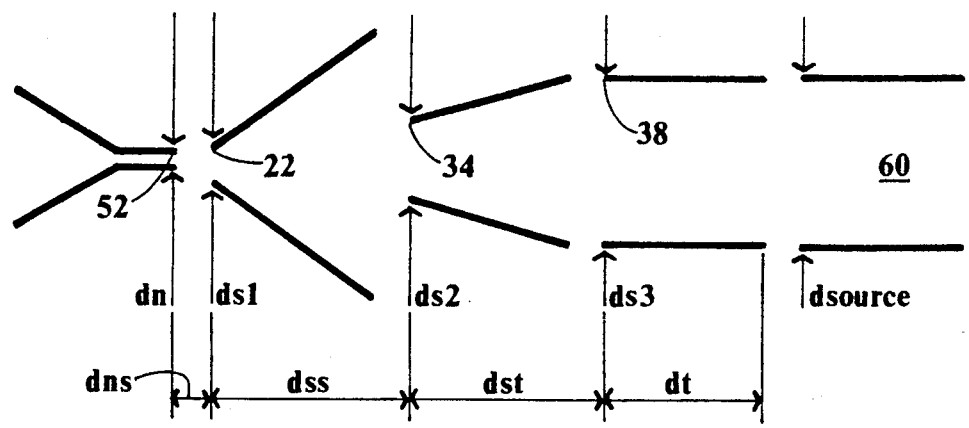
FIG._3.
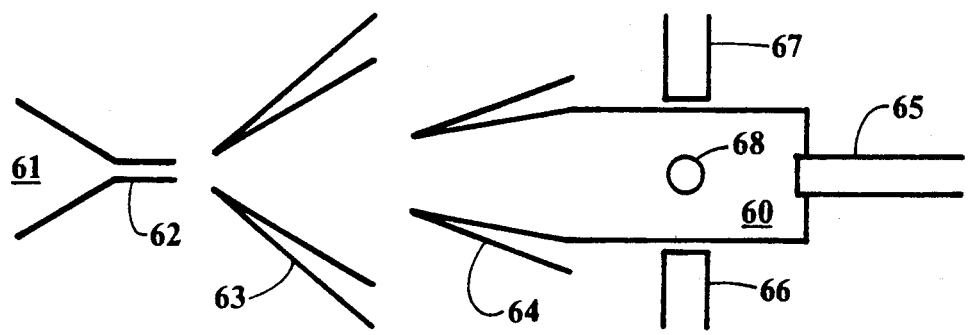
FIG._4.
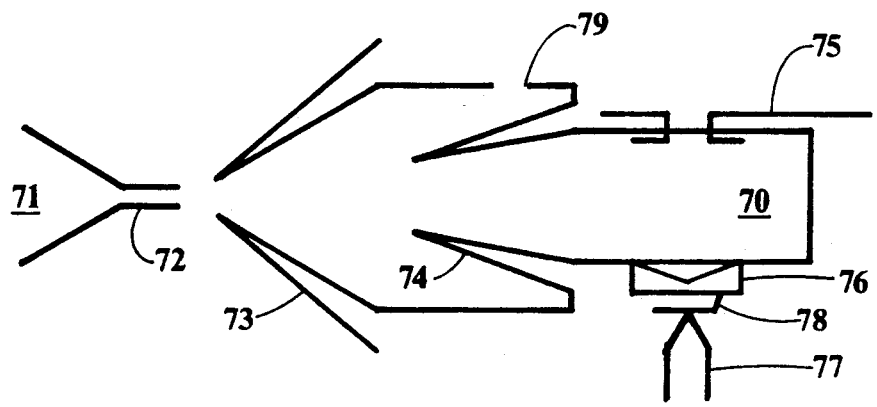
FIG._5.

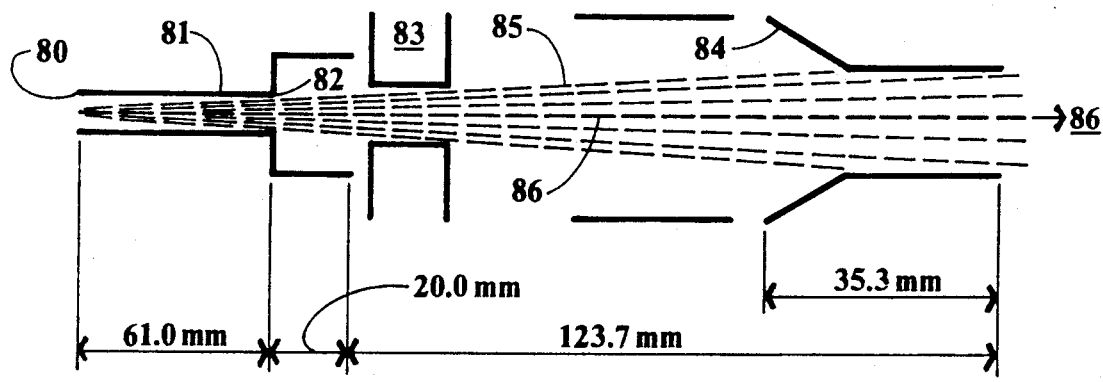
FIG.—6.
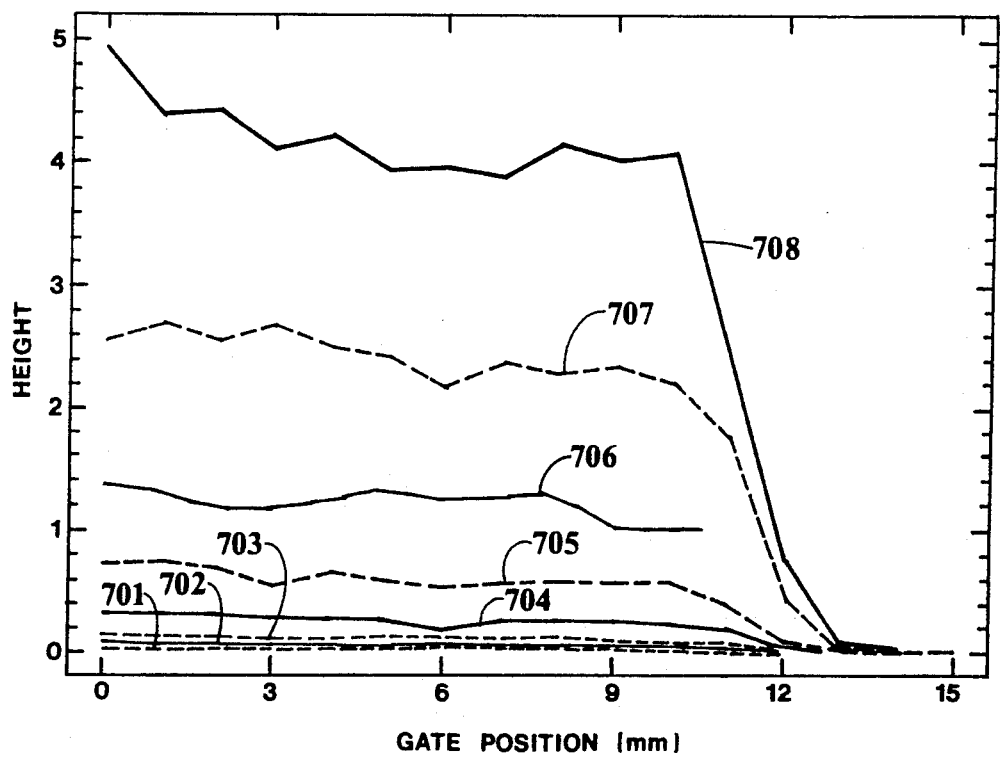
FIG.—7.

APPARATUS FOR INTERFACING LIQUID CHROMATOGRAPHY-MASS SPECTROMETRY SYSTEMS

FIELD OF THE INVENTION

This invention on relates generally to the introduction of samples into a mass spectrometry and more particularly to a method and interface device for separating desolvated particles from a stream of gas that are particularly suitable for use in combined liquid chromatography-mass spectrometry systems.

BACKGROUND OF THE INVENTION

Particle beam liquid chromatography mass spectrometry (PB LC/MS) is a relatively new analytical technique. In prior art PB LC/MS systems, an aerosol consisting of helium dispersion gas and droplets containing relatively low levels of analyte dissolved in LC effluent is first generated by a nebulizer. The aerosol is injected into a heated desolvation chamber where the volatile components of the droplets (primarily HPLC effluent) are vaporized, resulting in a mixture of helium gas, solvent vapor, and desolvation solvent particles. This mixture then enters a two stage momentum separator in which the less massive components (such as solvent vapor and helium gas) are pumped away while the more massive particles continue through the system on, what was believed to be, a more or less
. 2 straight line into the mass spectrometer source where the particles are vaporized, ionized, and mass analyzed. The momentum separator also serves as a pressure reduction and sample enrichment device, since most of the gas and solvent are pumped away, while most of the sample enters the mass spectrometer.

Browner et al., U.S. Pat. No. 4,629,478, issued Dec. 16, 1986, purports to describe a monodisperse aerosol generator which forms a stable jet of liquid at a velocity which allows columnar breakup into droplets of uniform size and spacing. Brandt et al , U.S. Pat. No. 4,863,491, issued Sep. 5, 1989, describes a multistage particle beam separator.

One problem encountered in the first generation of PB LC/MS instruments is poor linear response. Recent publications have shown that there is a systematic non-linearity in current instruments. See McLaughlin et al., "Particle Beam LC/MS for Drug Testing: Influence of Carrier Effect on Quantitation," paper 227, 6th (Montreux) Symposium on Liquid Chromatography/Mass Spectrometry; Behymer et al., "Liquid Chromatography/Particle Beam/Mass Spectrometry of Polar Components of Environmental Interest," *Anal. Chem.*, 62, 1990, 1686–1690; and Bellar et al., "Investigation of Enhanced Ion Abundances from a Carrier Process in High Performance Liquid Chromatography Particle Beam Mass Spectrometry," *J. Am. Soc. Mass Spectrom.*, 1, 1990, 92–98. Bellar and Behymer have referred to the problem as a "carrier effect" because the phenomena can also be seen as enhanced ion abundances in the presence of co-eluting components. This is the same as non-linearity, since non-linear behavior is a kind of self-carrier effect. These researchers have observed that by deliberately adding buffer to the mobile phase, a constant "co-eluting" component, the carrier effect is reduced and the linearity improves.

SUMMARY OF THE INVENTION

It is an object of the present invention to provide a more efficient and reliable PB LC/MS system with improved linearity in signal.

It is a further object of this invention to provide a compact PB LC/MS system with improved momentum separator transport efficiency and enhanced sensitivity.

It is a still further object of this invention to provide a PB LC/MS system wherein the source volume of the mass spectrometer is readily removable.

These and other objects are accomplished, in part, with the discovery that the "particle beam" emanating from the nozzle of the desolvation chamber is not a true collimated beam as previously assumed. Rather, the particles form an inhomogeneous conical dispersion or spread of particles with the largest ones concentrated near the center. The present invention comprises a PB LC/MS system wherein the skimmers of the momentum separator are designed to accommodate the conical dispersion so as to minimize the number of particles lost in the separator. In addition, in the inventive PB LC/MS devices, the exit of the momentum separator is very closely coupled to the entrance of the MS source volume. In one aspect of the invention, the exit of the second skimmer of the momentum separator and the entrance of the source volume can be the same orifice, although even a modestly close coupled system results in markedly improved linear response.

In another aspect of the invention, the momentum separator and source entrance are constructed as an unit so that the surfaces of the source volume, including the repeller and draw out lens, come into contact with samples or solvents The source volume can be easily withdrawn from the MS vacuum system without venting the vacuum to atmosphere. The source volume can then cleaned and/or replaced Different source volume designs can be readily interchanged for optimal conditions for Electron Impact (EI) or Chemical Ionization (CI) operation.

BRIEF DESCRIPTION OF THE DRAWINGS

FIG. 1 is a cross-sectional view of a particle beam interface.

FIG. 2 is a cross-sectional view of the skimmers of a momentum separator.

FIG. 3 is a cross-sectional view of a momentum separator.

FIG. 4 is a cross-sectional view of a schematic of an interface that is close coupled to the source volume of a mass spectrometer.

FIG. 5 is a cross-sectional view of a schematic of an interface that is close coupled to the source volume of a mass spectrometer FIG. 6 is a cross-sectional view of a schematic of an interface with a gate valve.

FIG. 7 is a graph of signal versus gate valve position.

DETAILED DESCRIPTION OF THE INVENTION

Hitherto it was believed that with the PB LC/MS technique, the "particle beam" which resulted from the supersonic jet expansion in the initial nozzle section of the momentum separator was a substantially perfectly collimated beam of monodispersed droplets See Willoughby and Browner, "Monodisperse Aerosol Generation Interface for Combining Liquid Chromatography with Mass Spectrometry," Anal. Chem., 56, 1984, 2626-2631. Experiments with the present invention establish that the above assumption is incorrect.

It is believed that nonlinear behavior in prior art PB LC/MS systems is, in part, the result of particle size discrimination by the momentum separator. This discrimination occurs even if it is assumed that the aerosol entering the desolvation chamber is "monodispersed", that is, all droplets are precisely that same size. The reason is that when analytes are introduced into the system at different concentrations, the particles derived form desolvated monodispersed droplets with varying analyte concentrations will be polydispersed. A momentum separator (which is a vacuum system) has a practical size cut-off level so that small particles are subject to removal. This is particularly the case when the analyte concentration is low.

The following calculations show how the particle size will vary with sample concentration.

(1) Particle Mass:

$$\text{Weight } (W_p) = \frac{\pi}{6} D_{droplet}^3 \times \text{Concentration } (C)$$

(2) Particle volume (assuming that particle density is equal to bulk density):

$$V_{particle} = \frac{W_p}{\rho_p}$$

(3) Particle Diameter:

$$d_p = \sqrt[3]{\frac{6 V_p}{\pi}}$$

$$d_p = \sqrt[3]{\frac{6 W_p}{\rho_p \pi}}$$

$$d_p = D_{droplet} \sqrt[3]{\frac{C}{\rho_p}}$$

For the above equations, $W_p$ is the particle weight, $D_{droplet}$ is the droplet diameter, $V_{particle}$ is the particle volume, $\rho_p$ is the particle density, and $D_p$ is the particle diameter.

As is apparent, the particle diameter is directly proportional to the droplet diameter and the particle diameter is proportional to the cube root of the concentration. It is expected that the supersonic jet generated t the momentum separator nozzle will have larger particles near the axis with smaller particles on the outside. In addition, as the particle size decreases, the "particle beam" will spread out even more.

The actual phenomenon which results in this cut-off level may involve the skimmers int he momentum separator or it may involve the fact that the particle beam itself has a small but finite divergence angle which results in a conical spread of particles inhomogeneous in particle size, that is, the larger particles are concentrated int he center, while the small particles are on the periphery. If the particle beam is required to transmit particles over a distance, the outside smaller particles can be lost against the transfer conduit walls. Thus, at lower levels, there would be a lower than expected response.

Referring to FIG. 1, a cross-sectional view of the particle beam interface of this invention is shown. This system comprises nebulizer 2 where the liquid solution is broken into droplets, desolvation chamber 4 where the solvent is evaporated, leaving particles which might contain traces of residual solvent, and momentum separator 6 where the particles are further desolvated and separated from solvent vapors, in preparation for ionization. The nebulizer 2 projects a stream of solvent droplets 8 into a cylindrical chamber 10. Here the solvent is evaporated, leaving an aerosol or suspension of particles containing a small proportion of residual solvent.

The mixture of solvent vapors, gases and desolvated particles is collected by the tapered collector side 12 of the nozzle plate 14 and, by means of the pressure drop across the nozzle, is projected through the nozzle 16 as a supersonic jet. The nozzle passageway 46 has inner diameter $(d_n)$ and outlet 52. The higher mass particles tend to concentrate near the center of the axis of the jet with the lower mass gas molecules further from the axis, thus forming a "particle beam." As shown in FIG. 2, the "particle beam" in actuality comprises an inhomogeneous conical dispersion or spread 51 of particles with the largest ones concentrated at its center along central axis 50. The angle of dispersion and the distribution of particles within the dispersion will vary.

The gas and particle mixture is passed through a series of chambers in the momentum separator of this invention, each chamber having a stronger vacuum than the preceeding chamber. The term "downstream", as used herein, is defined to mean the direction of material flow from weaker vacuum to stronger vacuum. The particles (or dispersion) travel into and through the first stage chamber 18 of the momentum separator 6 where more of the solvent vapors and other gases are removed from the mixture. The first stage skimmer 20 has a central axial opening or aperture 22 of sufficient diameter $(d_{s1})$ so that the conical dispersion 51 is not deflected by the skimmer. The gases are deflected by the conical surface 24 of the first skimmer 20.

Upon exiting the first stage chamber, the dispersion enters into the second stage chamber 30 where the gases are further expanded and separated from the particles. The dispersion 51 continues to travel through the axial, central opening 34 of the second skimmer 32. The gases are deflected by the conical surface 36 of the second skimmer 32. Orifice 34 is of sufficient diameter $(d_{s2})$ so that the conical dispersion 51 is not deflected by the skimmer. Thereafter, the dispersion traverses a short passageway or transfer tube 42 before entering the source volume of a mass spectrometer. In this close coupled configuration as shown in FIG. 1, the transfer tube is relatively wide and short so that the dispersion does not come into contact with the walls of the tube. Moreover, the entrance 38 of the source volume 60 is also wide enough to "capture" the entire dispersion.

Referring to FIG. 3, the separation distances between the nozzle outlet 52 and aperture 22, aperture 22 and aperture 34, and aperture 34 and the entrance 38 of the transfer tube are designated $d_{ns}$, $d_{ss}$, and $d_{st}$, respectively. The transfer tube has a diameter $d_{s3}$ and a length $d_t$; and the entrance of the source volume 60 has a diameter $d_{source}$. As is apparent, $d_n < d_{s1} < d_{s2} < d_{s3}$. In the embodiment shown in FIG. 3, the transfer tube is not attached to the entrance of the source volume of the mass spectrometer. In the close couple system of FIG. 1, the transfer tube is attached to the entrance. In another close coupled embodiment described below, the transfer tube can be effectively eliminated altogether.

In the design of prior art PB LC/MS systems, because the "particle beam" was considered more or less a collimate beam, the skimmers and source entrance were not adequately constructed to take into consideration the conical dispersion of particles. The loss of particles in the momentum separator and in the transfer tube contributed to the non-linear response in prior art systems. Specifically, in prior art designs, the diameters of the skimmer apertures were often too small (or either $d_{ns}$, $d_{ss}$, or $d_{st}$ was too long) to accommodate dispersion. Moreover, the transfer tube between the momentum separator and the relatively small diameter source volume entrance aperture further contributed to the problem. The result was that with prior art PB LC/MS systems, small particles are lost due to deflection by the skimmers, impact with the transfer tube walls, and blockage by the small source entrance.

The inventive PB LC/MS employs a momentum separator wherein the skimmers are configured so that the size of each aperture is large enough to encompass the periphery of the dispersion cone. In addition, the exit of the second skimmer can be closely coupled to the mass spectrometer source entrance. This minimizes the diameter of the dispersion cone section at the source entrance thereby allowing a maximum proportion of smaller particles to enter the source. As is apparent, the skimmer aperture and source entrance diameters are arranged in increasing proportions so that the largest proportion of the dispersion cone can be included. However, this requires that the vacuum system and liquid solution flow rate be adjusted so that the increasing orifice size does not result in too high a source pressure.

Another embodiment of the inventive device with close coupling, shown schematically in FIG. 4, comprises a desolvation chamber 61 with nozzle 62, and a momentum separator. Source volume 60 is an integral part of the momentum separator, which includes skimmers 63 and 64. This configuration allows the entire source volume to be removed through a vacuum port. The source volume includes hot target 65, filament 66, and repeller and entrance lens (collectively, 68 in plane). The ions are directed to target 67. In this embodiment, the second skimmer 64 could be an orifice in the source wall. The skimmer orifice and source entrance diameters are arranged in increasing proportions so that the largest proportion of the dispersal cone is included.

The device in FIG. 5 is similar to the embodiment of FIG. 4 and comprises desolvation chamber 71 with nozzle 72 and a momentum separator that includes skimmers 73 and 74. Gases are pumped out from the second stage chamber through opening 79. However, as is apparent, the source volume 70 is different with regard to some of its internal structures, namely: entrance lens 75, repeller 76, electrical connection for repeller 77, and ski-like contact 78.

With the present invention, close coupling results in improved linear response, but source fouling remains a problem. PB LC/MS, especially systems employing chemical ionization with methane, results in rapid source performance deterioration due to fouling of the source. Furthermore, use of non-volatile particles (e.g., buffers) aggravates the fouling. The embodiments as shown in FIGS. 4 and 5 permits the entire source volume to be conveniently removed for replacement or cleaning.

In the above embodiments, each device comprised a momentum separator that had two vacuum chambers. However, momentum separators with only one vacuum chamber or with three or more vacuum chambers can also be employed. In each vacuum chamber, the skimmer orifice must be of sufficient construction to accommodate the dispersion cone. Finally, the momentum separator should be closely coupled to the source assembly entrance.

As stated previously, one aspect of the present invention is the discovery that the "particle beam" emanating from the initial nozzle of the momentum separator is not a true collimated beam. To confirm this, a gate valve was positioned between the second skimmer and the source entrance of a mass spectrometer to show the expansion angle of the particle beam.

For this experiment, a standard Hewlett-Packard (Palo Alto, Calif.) HP5989 Particle Beam LC/MS in which the isolation valve between the particle beam interface and the mass spectrometer vacuum manifold was replaced with a 10 mm wide VAT gate valve. Except for the presence of the gate valve, the instrument was operated in a standard fashion. Samples (cortisol in methanol) were injected into a mobile phase of methanol at 0.4 ml/min in a Flow Injection Analysis (FIA) mode (i.e., no chromatography column present). A HP1090 HPLC was used to deliver the liquid flows and to make 1 μl sample injections at different concentrations. The particle beam nebulizer was adjusted to optimize the signal in a normal way. The helium flow was approximately 2 L/min and the nebulizer fused silica capillary was adjusted to slightly extend past the nebulizer capillary. The desolvation chamber was at approximately 45° C. FIG. 6 shows the axial measurements for the system wherein the particle beam enters aperture 80 of the second skimmer 81 and exits at aperture 82. Dispersion cone 85 is formed about central axis 86. As depicted, the source entrance cone 84 blocks some of the particles of the dispersion cone from entering mass spectrometry source volume 86. The position of gate valve 83 ranged from 0 (fully opened) to 15 (closed).

FIG. 7 shows the effect of closing the gate valve on the signal for samples at different concentrations ranging from approximately 7.81 to 1000 ng/ml. Curves 701, 702, 703, 704, 705, 706, 707 and 708 correspond to 7.51, 15.62, 31.25, 62.5, 125, 250, 500 and 1000 ng/ml respectively. The y axis is the signal height, the x axis is the position of the gate valve. "Height" refers to the peak height in arbitrary signal counts of a peak profile corresponding to an injected sample probe.

As is apparent, by closing the gate valve, the signal was attenuated as the gate passed the expansion cone of the particle beam. Indeed, the amount of closure required for the effect to set in comports with data regarding the conical solid angle which was ultimately determined by what can pass through the orifice in the source.

The gate valve experiment was repeated with a Particle Beam LC/MS system entitled the "pretty close coupled 5989" prototype in which the mass spectrometer source is brought closer to the particle beam interface. A standard HP5989 PB LC/MS was used but with all connection valving between the particle beam interface and the mass spectrometer source removed. The particle beam interface was replaced with a prototype in which the standard skimmers were mounted as close to the mass spectrometer vacuum manifold wall as possible. This had the effect of making this prototype approximately 15 cm closer coupled than the standard system.

With this "pretty close coupled" system, it was found that the cut-off is sharper which indicates that the expansion cone solid angle is intercepted closer to its vertex at the exit of the second skimmer.

It is to be understood that while the invention has been described above in conjunction with preferred specific embodiments, the description and examples are intended to illustrate and not limit the scope of the invention, which is defined by the scope of the appended claims.

We claim:

1. A liquid chromatography-mass spectrometry particle separator comprising:
   a vacuum chamber;
   means for introducing a mixture of solvent gas and particles into said vacuum chamber wherein said introduction means includes a nozzle of diameter $d_{nz}$ through which said mixture is projected as a supersonic jet into said vacuum chamber
   a skimmer having an aperture of sufficient construction so that substantially all the particles in said supersonic jet travel through said aperture which has a diameter $d_1$ wherein $d_1$ is greater than $d_{nz}$; and
   a mass spectrometer downstream of said skimmer and having a source assembly with an entrance which has a diameter $d_s$ wherein $d_s$ is greater than $d_1$, said aperture being positioned adjacent to said source assembly entrance so that substantially all the particles in said supersonic jet pass through said entrance and into said source assembly.

2. The liquid chromatography-mass spectrometry particle separator as defined in claim 1 wherein said skimmer comprises a conical surface which radially narrows to an apex opposed to said introduction means with said skimmer aperture in said apex.

3. The liquid chromatography-mass spectrometry particle separator comprising: means for introducing a mixture of solvent gas and particles into said vacuum chamber wherein said introduction means includes a nozzle of diameter $d_{nz}$ through which said mixture is projected as a supersonic jet into said vacuum chamber;
   a skimmer having an aperture of sufficient construction so that substantially all the particles in said supersonic jet travel through said aperture which has a diameter $d_1$ wherein $d_1$ is greater than $d_{nz}$ and wherein aid skimmer comprises a conical surface which radially narrows to an apex opposed to said introduction means with said skimmer aperture in said apex; and
   a mass spectrometer downstream of said skimmer and having a source assembly with an entrance which has a diameter $d_s$, wherein $d_s$ is greater than $d_1$, and wherein said aperture is attached to said source assembly entrance so that substantially all the particles in said supersonic jet pass through said entrance and into said source assembly.

4. The liquid chromatography-mass spectrometry particle separator comprising:
   a first vacuum chamber;
   means for introducing a mixture of solvent gas and particles into said first vacuum chamber wherein said introduction means includes a nozzle of diameter $d_{nz}$ through which said mixture is projected as a supersonic jet into said first vacuum chamber;
   a first skimmer having a first aperture of sufficient construction so that substantially all the particles in said supersonic jet travel through said first aperture which has a diameter $d_1$;
   a second vacuum chamber downstream of and communicating with said first aperture;
   a second skimmer having a second aperture of sufficient construction so that substantially all the particles in the supersonic jet travel through said second aperture which has a diameter $d_2$; and
   a mass spectrometer downstream of said second skimmer and having a source assembly with an entrance which has a diameter $d_2$, wherein $d_2 > d_2 > d_1 > d_{nz}$, said second aperture being positioned adjacent to said source assembly entrance so that substantially all the particles in the supersonic jet pass through said entrance and into said source assembly.

5. The liquid chromatography-mass spectrometry particle separator as defined in claim 4 wherein said first skimmer comprises a first conical surface which radially narrows to a first apex opposed to said introduction means and wherein said second skimmer comprises a second conical surface which radially narrows to a second apex opposed to said introduction means, said second skimmer being downstream of said second vacuum chamber so that particles exit said second vacuum chamber through said second aperture.

6. A liquid chromatography-mass spectrometry particle separator comprising:
   a first vacuum chamber;
   means for introducing a mixture of solvent gas and particles into said first vacuum chamber wherein said introduction means includes a nozzle of diameter $d_{nz}$ through which said mixture is projected as a supersonic jet into said first vacuum chamber;
   a first skimmer having a first aperture of sufficient construction so that substantially all the particles in said supersonic jet travel through said first aperture which has a diameter $d_1$;
   a second vacuum chamber downstream of and communicating with said first aperture;
   a second skimmer having a second aperture of sufficient construction so that substantially all the particles in said supersonic jet travel through said second aperture which has a diameter $d_2$;
   a mass spectrometer downstream of said second skimmer and having a source assembly with an entrance which has a diameter $d_s$ wherein $d_s > d_2 > d_1 > d_{nz}$, said second aperture being positioned adjacent to said source assembly entrance so that substantially all the particles int he supersonic jet pass through said entrance and into said source assembly;
   wherein said first skimmer comprises a first conical surface which radially narrows to a first apex opposed to said introduction means and wherein said second skimmer comprises a second conical surface which radially narrows to a second apex opposed to said introduction means, said second skimmer being downstream of said second vacuum chamber so that particles exit said second vacuum chamber through said second aperture; and
   wherein said second aperture is attached to said source assembly entrance.

7. A liquid chromatography-mass spectrometry particle separator comprising:

a plurality of vacuum chambers designated $vc_1$, $vc_2$ ... $vc_n$, said vacuum chambers arranged in series so that $vc_1$ is in communication with $vc_2$, $vc_2$ is in communication with $vc_3$ and so on, wherein each vacuum chamber contains a skimmer having an aperture of sufficient construction to permit particles to pass through wherein the aperture of $vc_1$ has a diameter $d_1$ and wherein the aperture of $vc_2$ has a diameter $d_2$, and so on, so that the aperture of $vc_n$ has a diameter $d_n$;

means for introducing a mixture of solvent gas and particles into said $vc_1$ wherein said introduction means includes a nozzle of diameter $d_{nz}$ through which said mixture is projected as a supersonic jet into said $vc_1$; and a mass spectrometer downstream of said $vc_n$ and having a source assembly with an entrance that has a diameter $d_2$, wherein $d_s > d_n > \ldots > d_2 > d_1 > d_{nz}$ and wherein the entrance is positioned adjacent to the aperture of said $vc_n$ so that substantially all the particles in the supersonic jet pass through said entrance and into said source assembly.

8. The liquid chromatography-mass spectrometry particle separator as defined in claim 7 wherein each skimmer comprises a conical surface which radially narrows to an apex opposed to said introduction means and wherein the aperture in $vc_n$ is attached to the source assembly entrance.

9. The particle separator as defined in either claim 1, 2, 3, 4, 5, 6, 7, or 8 wherein said source assembly is removable.

* * * * *